United States Patent [19]

Rosiere

[11] 4,012,203
[45] Mar. 15, 1977

[54] GAS GENERATING APPARATUS FOR USE WITH CULTURE TRANSPORT AND STORAGE

[75] Inventor: Charles Eugene Rosiere, East Aurora, N.Y.

[73] Assignee: Marion Laboratories, Inc., Kansas City, Mo.

[22] Filed: Jan. 30, 1976

[21] Appl. No.: 654,027

[52] U.S. Cl. ............................................. 23/282
[51] Int. Cl.² .......................................... B01J 7/02
[58] Field of Search ............. 23/282; 195/109, 127

[56] References Cited

UNITED STATES PATENTS

| | | | |
|---|---|---|---|
| 3,100,692 | 8/1963 | Wachter | 206/84 X |
| 3,246,959 | 4/1966 | Brewer | 23/282 |
| 3,448,011 | 6/1969 | Russomanno | 195/142 X |
| 3,615,252 | 10/1971 | Di Pietro | 23/282 |
| 3,890,102 | 6/1975 | Gathmann et al. | 23/282 |

*Primary Examiner* — Joseph Scovronek
*Attorney, Agent, or Firm* — Merriam, Marshall, Shapiro & Klose

[57] ABSTRACT

A gas generating apparatus comprising a container having an opening, a gas generating material in the container, an ampoule containing a liquid which is reactive with the gas generating material to produce a gas, said ampoule being openable from outside the container to free the liquid to contact the gas generating material, and means in the container which prevents liquid from flowing from the container after the ampoule is opened but which permits flow of gas generated in the container out of the container opening.

7 Claims, 3 Drawing Figures

GAS GENERATING APPARATUS FOR USE WITH CULTURE TRANSPORT AND STORAGE

This invention relates to disposable gas generating apparatus. More particularly, this invention is concerned with gas generating apparatus for use in collecting, transporting and storing bacterial cultures of the type which remain viable only when in the presence of a particular gaseous environment or atmosphere.

Many diseases of man and lower animals are bacterial in origin. The treatment of many bacterial diseases requires that the infecting organism be identified. A drug known to be effective against the infecting organism can then be prescribed.

The identification of an infecting organism is generally by means of a culture obtained from the patient or animal. The culture is then transported to a laboratory for determination of the identity of the infecting organism. Such laboratories require highly trained microbiologists and elaborate, expensive equipment. Suitable testing laboratories, accordingly, are not always readily available. It therefore becomes necessary for the patient to visit or animal to be taken to the laboratory where the culture can be obtained and put immediately into the test procedures or for the culture to be taken at a location remote from the laboratory and then transported to the laboratory for testing.

While the collecting of a culture generally presents no difficulties, the storage and/or transportation of the culture to a testing laboratory under conditions which guarantee the culture will be viable and free of contamination upon arrival presents serious problems. Although contamination from other organisms can generally be avoided by suitable means, the maintenance of a viable culture often requires, in addition to a suitable nutrient medium, the storage and transportation of the culture in a particular gaseous environment which promotes its viability.

There are some organisms which require special atmospheres for proper growth. Thus, organisms such as the gonococcus, menigococcus and brucella require a substantially higher concentration of carbon dioxide than that of the atmosphere for proper growth. Although this is generally known by bacteriologists, it is disclosed in Brewer U.S. Pat. No. 3,246,959.

The Brewer U.S. Pat. No. 3,246,959 discloses a gas-producing device for generating an atmosphere conducive for maintaining and increasing the viability of organisms which require a special non-toxic atmosphere. The patent shows the chemical generation of hydrogen, carbon dioxide and acetylene for the purpose of supplying a non-toxic atmosphere to a culture in a container.

Aronoff U.S. Pat. No. 3,773,035 and Patterson U.S. Pat. No. 3,750,646 each disclose culture collecting and transporting apparatus. The apparatus is used by collecting a culture on a swabbing tip and placing it in contact with a medium for sustaining the culture. The system of each patent is intended to maintain a carbon dioxide enriched atmosphere around the collected culture to promote its growth.

Although the prior art discloses culture collecting and transporting apparatus which provide a controlled gaseous atmosphere around a collected culture, there is a need for a convenient, efficient, low cost, disposable apparatus for generating a gas for use in controlling the atmosphere surrounding a collected bacterial culture.

According to the invention there is provided novel gas generating apparatus which includes a container having an opening, a gas generating material in the container, an ampoule containing a liquid which is reactive with the gas generating material to produce a gas, said ampoule being openable from outside the container to free the liquid to contact the gas generating material, and means in the container which prevents liquid from flowing from the container after the ampoule is opened but which permits flow of gas generated in the container out of the container opening.

The gas generating material in the container may be a material which, when contacted with the liquid in the ampoule, produces carbon dioxide or some other gas which provides an environment beneficial to a bacteria sample. The gas generating material may be in a solid or liquid form and it may be in a separate ampoule.

In a particular embodiment of the invention the container may be a flexible polymeric tube closed at one end and having an opening at the other end. The ampoule can fit snugly in the tube with the gas generating material located between the tube closed end and the ampoule. The ampoule is advisably one which can be opened by squeezing the tube to rupture or break the ampoule to release the liquid. The means to prevent flow of the liquid from the tube after the ampoule is opened may be positioned between the ampoule and the opening in the tube and it may take the form of an absorbent plug.

The invention will be described further in conjunction with the attached drawings, in which.

Figure 1:
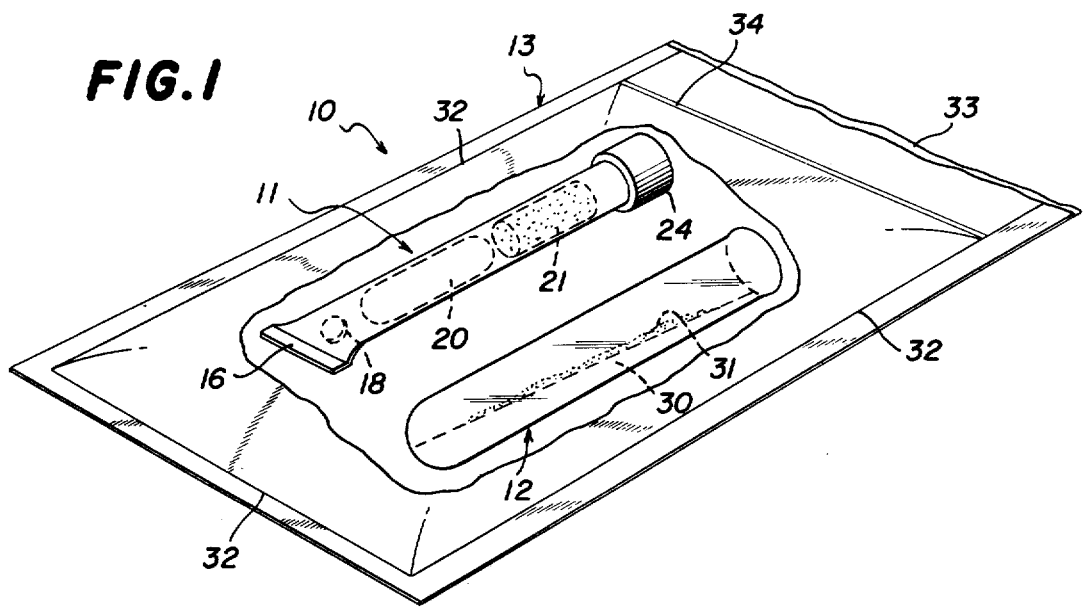
FIG. 1 is a perspective view of a package for transporting a bacteria culture and contains a gas generating apparatus provided by this invention.

With reference to FIG. 1, the bacteria culture transporting package 10 constitutes a gas generating apparatus 11, and a test tube 12 containing a bacteria culture, both placed inside of a pouch or bag 13.

The gas generating apparatus 11 comprises a container in the form of an elongated plastic tube 15 which is closed at end 16 and is open at end 17. The tube 15 may be made of a flexible but self-supporting polymeric material such as polyethylene, polypropylene or a polypropylene copolymer such as the one available as Avisun 6011.

One or more gas generating solid tablets or pellets 18 is positioned in tube 15 adjacent the closed end 16. The tablet 18 has a composition which is suitable for generating a gas, such as carbon dioxide.

Ampoule 19 is positioned in tube 15 more or less snugly so that it maintains its position. A liquid 20 is contained in ampoule 19. The composition of liquid 20 is selected so that it, when released from ampoule 19, will react with tablet 18 to generate a gas. The ampoule 19 can be made of glass or some other material which is nonreactive with liquid 20 or the components of gas generating tablet 18. The ampoule 19 is advisably made so that it will rupture or break upon application of finger pressure to the outside of tube 15 adjacent the ampoule wall. In this way the ampoule may be opened and the liquid 20 freed to react with tablet 18.

A liquid absorbent plug 21, such as of polyester fibers, is positioned in tube 15 after the ampoule 19 is placed in the tube. The absorbent plug 21 is thus located between the ampoule 19 and the tube open end 17 so that liquid cannot flow from the tube.

A polymeric cap 24 having a central hole 25 and a fibrous biological filter 26 is pressed firmly over the open end of tube 15. The filter 26 is made of a material which will permit gas generated in tube 15 to flow from the tube readily but which will remove bacteria which may be possibly present in tube 15 and which might otherwise escape during the flow of gas from the tube.

The gas generating tablet 18 may have the following composition when it is desired to produce carbon dioxide:

| | |
|---|---|
| Sodium bicarbonate | 52.5 mg. |
| Lactose DT | 47 mg. |
| Microporous cellulose--Avicel PH102 | 57.5 mg. |
| Tabletting lubricant--Calcium stearate | 2.0 mg. |

The ampoule 19 may contain as the liquid 20 one ml. of 0.45 N hydrochloric acid in a glass ampoule 1-13/16 inches long. It should be understood, however, that the size of ampoule 19 and the strength and quantity of liquid 20 in the ampoule are coordinated with the ingredients of tablet 18 so as to result in the generation of a predetermined volume of one or more gases.

The described gas generating apparatus 11 constitutes a disposable throw-away unit which is intended to be employed only once, such as for the production of carbon dioxide or a reducing gas or both such gases. It is particularly useful in culture collecting and transporting systems where it is considered advisable for an organism to remain viable to be surrounded by a carbon dioxide atmosphere. The gas generating apparatus is highly useful for generating a carbon dioxide atmosphere for use in transporting or storing bacteria cultures which require, or are most likely to remain viable longer, when placed in an atmosphere containing a substantial amount more of carbon dioxide, and less oxygen, than is found in the atmosphere. Since the gonococcus organism requires an atmosphere enriched with carbon dioxide the gas generating apparatus provided herewith is useful in conjunction with transporting a culture of this organism.

Figure 2:
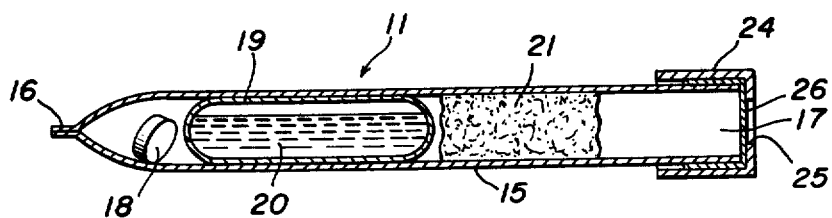
FIG. 2 is a longitudinal, axial cross-sectional view of the gas generating apparatus shown in FIG. 1.

Although the gas generating apparatus illustrated by FIG. 2 may be used in many ways to generate special atmospheric environments, one such way in which it may be employed is illustrated by FIG. 1. A test tube 12 containing an agar slant 30 with a gonococcus culture 31 growing thereon is placed in plastic pouch or bag 13. The bag 13 may be made of plastic flexible film or sheet material of low gas permeability. The bag 13 may be made of two sheets of plastic film heat sealed 32 around three-side edges, thereby leaving an open mouth 33 through which the tube 12 may be inserted into the bag. The gas generating apparatus 11 is then inserted into bag 13 and the mouth 33 is sealed shut in any suitable way, such as by means of heat seal 34.

The resulting package is then put in vertical position with the cap 24 in top position. The ampoule 19 is then broken by squeezing tube 15. The acid in the ampoule 19 is thereby released and flows into contact with tablet 18. Reaction of the acid with the sodium bicarbonate results in the generation of carbon dioxide. The gas flows through the entire length of tube 15 since plug 21 is gas permeable. Plug 21 absorbs excess acid and prevents it from flowing elsewhere in the tube. The liquid acid also combines with the ingredients of tablet 18 to form a slush which further serves to hold the liquid acid in place.

The bag 13 may be made from a transparent material of low gas permeability, such as a laminate identified as No. CL5040 (Clear Lam Products). As the carbon dioxide is generated in tube 15 the gas flows out opening 17 through filter 26 into bag 13. The generated gas causes the bag 13 to balloon or expand outwardly. The ballooning effect is evidence that the gas has generated as expected.

The chemical means suitable for generating the gaseous carbon dioxide in the apparatus of this invention is not to be limited to the specific embodiment set forth herein. Other well known chemical means for gaseous carbon dioxide generation may be used. Broadly, any material which upon contact with a liquid releases carbon dioxide in adequate amount in a reasonably short time may be used. The least expensive method, of course, is to contact a carbonate or bicarbonate salt with a dilute acid which will not produce vapors having an adverse effect on the culture. Instead of putting a dilute acid in the ampoule it can be filled with water, and sodium bicarbonate and citric acid, or some suitable acid salt, can be put in pellet 18 to generate carbon dioxide. Other feasible systems will appear readily to skilled chemists.

Figure 3:
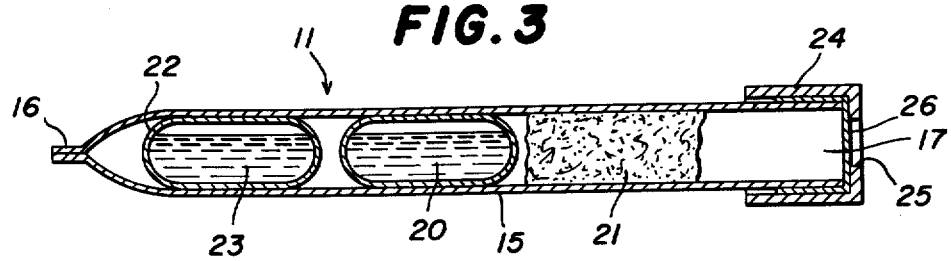
FIG. 3 is a gas generating apparatus like that of FIG. 2 but with liquid gas generating material in an ampoule.

FIG. 3 of the drawings shows a gas generating apparatus like that shown in FIG. 2 but with the solid gas generating material 18 of FIG. 2 replaced by an ampoule 22 containing a liquid gas generating material, such as a solution of sodium bicarbonate.

The foregoing detailed description has been given for clearness of understanding only, and no unnecessary limitations should be understood therefrom, as modifications will be obvious to those skilled in the art.

What is claimed is:

1. A gas generating apparatus comprising:
   an elongated flexible tube closed at one end and having an opening at the other end,
   a carbon dioxide generating material in the tube,
   an ampoule in the tube containing a liquid which is reactive with the carbon dioxide generating material to produce carbon dioxide, said ampoule being rupturable by squeezing the outside of the tube to free the liquid to contact the carbon dioxide generating material, and
   a plug located in the tube between the ampoule and the opening in the tube which prevents liquid from flowing from the tube after the ampoule is opened but which permits flow of the carbon dioxide gas generated in the tube out of the opening.

2. A gas generating apparatus according to claim 1 in which the gas generating material is a solid.

3. A gas generating apparatus according to claim 1 in which the liquid in the ampoule is water or aqueous acid and the gas generating material is reactive therewith to produce carbon dioxide.

4. A gas generating apparatus according to claim 1 in which the ampoule fits snugly in the tube and the gas generating material is between the tube closed end and the ampoule.

5. A gas generating apparatus according to claim 1 in which the tube is a polymeric material.

6. A gas generating apparatus according to claim 2 in which the gas generating solid material is a carbonate or bicarbonate salt.

7. A gas generating apparatus comprising:

an elongated flexible tube closed at one end and having an opening at the other end,
a gas generating material in the tube,
an ampoule in the tube containing a liquid which is reactive with the gas generating material to produce a gas, said ampoule being rupturable by squeezing the outside of the tube to free the liquid to contact the gas generating material, and
a plug located in the tube between the ampoule and the opening in the tube which prevents liquid from flowing from the tube after the ampoule is opened but which permits flow of the gas generated in the tube out of the opening.

* * * * *